US00PP08321P

United States Patent [19]

Kientzler

[11] Patent Number: Plant 8,321

[45] Date of Patent: Jul. 27, 1993

[54] IMPATIENS PLANT NAMED TOBAGO

[75] Inventor: Ludwig Kientzler, Gensingen, Fed. Rep. of Germany

[73] Assignee: Paul Ecke Ranch, Inc., Encinitas, Calif.

[21] Appl. No.: 872,420

[22] Filed: Apr. 23, 1992

[51] Int. Cl.[5] ..... A01H 5/00

[52] U.S. Cl. ..... Plt./87.6

[58] Field of Search ..... Plt./87.6

*Primary Examiner*—James R. Feyrer

*Assistant Examiner*—Erich Veitenheimer

*Attorney, Agent, or Firm*—Foley & Lardner

[57] ABSTRACT

A new and distinct cultivar of Impatiens plant name Tobago, characterized by its relatively large, coral flowers, compact growth habit with excellent self-branching without pinching, dark bronze-green foliage with red midveins, very early and uniform flowering, floriferous habit, and by its suitability to pot or hanging basket culture.

1 Drawing Sheet

The present invention relates to a new and distinct cultivar of plant known as Impatiens and commercially known as New Guinea Impatiens. The new cultivar is known by the cultivar name Tobago, and was developed by the inventor Ludwig Kientzler in Gensingen, Federal Republic of Germany by crossing the cultivar designated D-528 (seed parent) with the cultivar designated E-183 (pollen parent).

Asexual reproduction by terminal (stem tip) cuttings taken by me or under my supervision at Gensingen, Federal Republic of Germany, has shown that the unique features of this new impatiens are stabilized and are reproduced true to type in successive propagations.

The following characteristics distinguish the new impatiens from both its parent varieties and other cultivars of this general type known and used in the floriculture industry:

1. Compact growth habit with good self-branching characteristics. Plants in 16.5 cm pots were 16.5 cm tall and 30 cm wide, eight weeks after planting.

2. Large coral flowers. Open flowers measure more than 5.5 cm in diameter.

3. Early flowering and floriferous. Plants in 16.5 cm pots were in flower 7 weeks after planting.

4. Dark bronze-green foliage with red midveins. Leaf surface is scabrous.

5. Well suited both to 4" pot and 8" hanging basket culture.

Tobago can be compared in certain respects to the cultivar Melissa, disclosed in a pending application of applicant. The flower color of Tobago is generally similar to Melissa, but the color of Melissa is much deeper. The growth habit of Tobago is more compact. Eight weeks old plants of Melissa were 20 cm tall and 33 cm wide, compared to the dimensions of Tobago as noted above.

The accompanying colored photograph is a top perspective view of the new cultivar, showing color as true as it is reasonably possible to obtain in a colored reproduction of this type.

The following is a detailed description of my new impatiens cultivar based on plants grown under commercial practice in Encinitas, Calif. Plants were started as rooted cuttings and were transplanted in mid-December into 16.5 cm (6.5 inch) pots, one pot per plant. By mid-February, plants were growing vigorously and were in flower. The values, measurements and observations noted below were taken from plants in full bloom in mid-February.

Color references are made to The Royal Horticultural Society Colour Chart (R.H.S.), except where general terms of ordinary dictionary significance are used.

Parentage: Cross between D-528 (seed) and E-183 (pollen).

Asexual reproduction:

A. *Cutting type.*—Tip, with stems 2–3 cm long developing to 4–5 cm after 21 days in propagation.

B. *Time to initiate roots.*—8–10 days at 23° C.; nicely developed root mass in 18–21 days.

C. *Rooting habit.*—Numerous, fibrous, adventitious roots from the stem.

Plant description:

A. *Form.*—Symmetrical, bush shaped, flowering herb, with self-branching characteristics giving the plant a full appearance. Pinching is not recommended since it does not enhance branching and only delays flowering by removing flower buds.

B. *Habit of growth.*—Vigorous, self-branching habit, producing whorls of leaves and flowers. Growth is indeterminate and flowering is continuous.

C. *Foliage description.*—Leaves are simple. Lower leaves on stems are opposite. Higher leaves in whorls of 3–5, but predominately 5. 1. Leaf shape: Ovate. Leaf blade tips are acuminate; bases are acute. 2. Leaf blade size: Mature leaves typically 10 cm long and 4 cm wide. 3. Petiole length: About 3 cm. 4. Leaf margin: Ciliated and finely serrated. 5. Leaf texture: Slightly rugose and hirsutulous. a. Upper surface: Scabrous. b. Under surface: Glabrous. 6. Leaf color: Dark bronze-green with red midvein. a. Upper surface: Darker than 147A. b. Under surface: Greyed-purple, near 183A to 183B. 7. Venation: Pinnate.

Flowering description:

A. *Flowering habits.*—Very floriferous. Flowering is continuous. Flowers develop progressively around the whorl of leaves, taking 5–7 days from buds which show color, to bloom. Flowers are single and large, lasting for 2–3 weeks.

B. *Natural flowering season.*—Flowering is indeterminate and occurs throughout the year. Quantity of flowers increases with increasing light intensity and duration. However, floriferousness may wane during hot summer days in temperate climates.

C. *Flower buds.*—Ellipsoidal and covered with 3 sepals plus 2 rudimentary sepals fused into the under surface of the superior petal. A spur originates from the base of the inferior sepal. Spur is reddish and approximately 5 cm long.

D. *Flowers borne.*—Singly, on reddish pedicels about 6 cm long.

E. *Quantity of flowers.*—Two (2) flowers per leaf. Flowers occur progressively around the whorl of leaves so that tight buds to mature flowers are visible at the same time.

F. *Petals.*—Petals open nearly perpendicular to the pedicel so the plane of the flower surface is nearly flat. 1. Number of petals: Five (5) petals, all overlapping. 2. Shape: All petals are heart-shaped. Superior petal has a broad base. Other petals have a pointed base. 3. Color: Coral. a. Upper surface: Darker than 43D. b. Under surface: Near 48C. 4. Flower size: Up to 6 cm in diameter.

G. *Reproductive organs.*—Flowers are monoecious. 1. Stamens: Five (5), broad and fused to form a tube around the ovary; tinged with red. 2. Anther: Hooded and cream colored. 3. Pollen: Cream colored. 4. Stigma: Five pointed star, colorless. 5. Styles: Very short. 6. Ovary: 5-celled, 4–5 mm long until fertilized. Grows to 1 cm or longer after fertilization; green.

Resistance to disease: Good resistance to common stem and root disease, Rhizoctonia and Pythium. Botrytis may be a problem in humid or mist propagation environments, but no greater than with other New Guinea Impatiens cultivars.

I claim:

1. A new and distinct cultivar of Impatiens plant named Tobago, as illustrated and described.

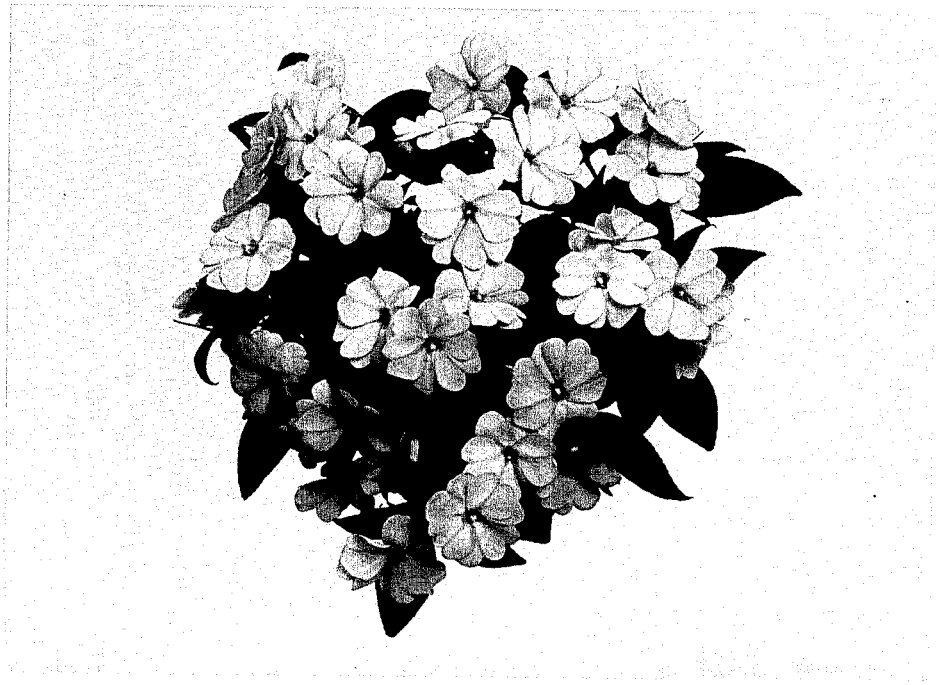

* * * * *